(12) United States Patent
Patterson et al.

(10) Patent No.: US 11,138,235 B1
(45) Date of Patent: Oct. 5, 2021

(54) SYSTEMS AND METHODS FOR DATA CATEGORIZATION AND DELIVERY

(71) Applicant: WELLNESS COACHES USA, LLC, Blue Bell, PA (US)

(72) Inventors: Daniel Patterson, Shorewood, MN (US); Michael Larkin, St. Louis, MN (US); Jason Childs, Rosemount, MN (US); Mike Reier, Minnetrista, MN (US)

(73) Assignee: WELLNESS COACHES USA, LLC, Blue Bell, PA (US)

(*) Notice: Subject to any disclaimer, the term of this patent is extended or adjusted under 35 U.S.C. 154(b) by 1235 days.

(21) Appl. No.: 15/093,284

(22) Filed: Apr. 7, 2016

Related U.S. Application Data

(63) Continuation-in-part of application No. 13/906,760, filed on May 31, 2013, now Pat. No. 9,727,885, which is a continuation of application No. 13/831,294, filed on Mar. 14, 2013, now abandoned.

(60) Provisional application No. 61/670,714, filed on Jul. 12, 2012.

(51) Int. Cl.
*G06F 16/28* (2019.01)
*G16H 40/63* (2018.01)

(52) U.S. Cl.
CPC .......... *G06F 16/285* (2019.01); *G06F 16/288* (2019.01); *G16H 40/63* (2018.01)

(58) Field of Classification Search
CPC .... G06F 19/3481; G06F 19/00; G06F 16/285; G06F 16/288; G06Q 50/22; A61B 5/0022; G16H 40/63

USPC ..................................................... 705/2–3
See application file for complete search history.

(56) References Cited

U.S. PATENT DOCUMENTS

| | | | |
|---|---|---|---|
| 9,727,885 B1 | 8/2017 | Reier | |
| 2007/0050215 A1 | 3/2007 | Kil et al. | |
| 2007/0122780 A1 | 5/2007 | Moon et al. | |
| 2008/0033581 A1* | 2/2008 | Doshi | A63B 71/06 700/92 |
| 2008/0086318 A1 | 4/2008 | Gilley et al. | |
| 2008/0262866 A1 | 10/2008 | Greene | |
| 2009/0319347 A1 | 12/2009 | Albrecht | |
| 2012/0313776 A1 | 12/2012 | Utter, II | |

(Continued)

OTHER PUBLICATIONS

Anonymous, An Intelligent Self-Adapted Layout Designer, Mar. 28, 2008, IP.com, pp. 1-7, https://ip.com/IPCOM/000168813 (Year: 2008).*

(Continued)

*Primary Examiner* — Joy Chng
(74) *Attorney, Agent, or Firm* — Schwegman Lundberg & Woessner, P.A.

(57) ABSTRACT

Disclosed in some examples are systems, methods, and machine-readable media for improved information systems. These improved information systems provide a technical solution that includes a predictive learning system and improved data analysis. The data analysis processes multiple data input streams simultaneously, and applies digital signal processing to identify correlation between or among multiple data input streams. The user interface is used to present outputs according to personalized data profile characteristics. In some examples, the user interface includes multiple information cards that are formatted and prioritized based on relevance or urgency.

20 Claims, 12 Drawing Sheets

(56) References Cited

U.S. PATENT DOCUMENTS

| | | | | |
|---|---|---|---|---|
| 2012/0317167 | A1* | 12/2012 | Rahman | A61B 5/02055 709/202 |
| 2013/0225370 | A1* | 8/2013 | Flynt | A63B 71/0622 482/4 |
| 2018/0082317 | A1 | 3/2018 | Reier | |

OTHER PUBLICATIONS

Subramanya et al., User Interfaces For Mobile Content, Apr. 1, 2006, Computer, vol. 39, Issue: 4, pp. 85-87, DOI: 10.1109/MC.2006.144 (Year: 2006).*
"U.S. Appl. No. 15/636,000, Preliminary Amendment filed Dec. 13, 2017", 7 pgs.
"U.S. Appl. No. 13/906,760, Appeal Brief filed Apr. 7, 2016", 26 pgs.
"U.S. Appl. No. 13/906,760, Examiner Interview Summary dated Jan. 20, 2017", 3 pgs.
"U.S. Appl. No. 13/906,760, Examiner Interview Summary dated Apr. 1, 2015", 3 pgs.
"U.S. Appl. No. 13/906,760, Final Office Action dated Oct. 8, 2015", 12 pgs.
"U.S. Appl. No. 13/906,760, Non Final Office Action dated Mar. 10, 2015", 11 pgs.
"U.S. Appl. No. 13/906,760, Non-Final Office Action dated Oct. 20, 2016", 15 pgs.
"U.S. Appl. No. 13/906,760, Response filed Mar. 20, 2017 to Non Final Office Action dated Oct. 20, 2016", 23 pgs.
"U.S. Appl. No. 13/906,760, Response filed Sep. 9, 2015 to Non-Final Office Action dated Mar. 10, 2015", 19 pgs.
Intelliprev, "Intelliprev Homepage", http://www.intelliprev.com/homepage.htm.
Intelliprev, "Intelliprev: A primer", http://organizationalwellness.com/wp-content/uploads/2013/02/1.IntelliPrevT_Primer.pdf.
Intelliprev, "Prevention Program Library (Overview) Introductory Research Note (1/3)", http://www.intelliprev.com/library_oveiview.cfm?sc=0.
Intelliprev, "Prevention Program Library (Overview) Introductory Research Note (2/3)", http://www.intelliprev.com/library_overview.cfm?sc=0.
Intelliprev, "Prevention Program Library (Overview) Introductory Research Note (3/3)", http://www.intelliprev.com/library_overview.cfm?sc=0.
US Health Center, Inc., "Health Management Programs—Science and Technology", http://ushcinc.com/science-technology.html last visited (Nov. 26, 2013).
US Health Center, Inc., "Homepage", http://ushcinc.com last visited (Nov. 26, 2013).
US Health Center, Inc., "Personal Health Management—Products and Services", http://ushcinc.com/PHM-services.html last visited (Nov. 26, 2013).
"U.S. Appl. No. 13/906,760, Notice of Allowance dated Jun. 23, 2017", 9 pgs.
"U.S. Appl. No. 15/636,000, Examiner Interview Summary dated Apr. 14, 2020", 3 pgs.
"U.S. Appl. No. 15/636,000, Non Final Office Action dated Jan. 6, 2020", 15 pgs.
"U.S. Appl. No. 15/636,000, Final Office Action dated Aug. 7, 2020", 16 pgs.
"U.S. Appl. No. 15/636,000, Response filed May 6, 2020 to Non Final Office Action dated Jan. 6, 2020", 14 pgs.
"U.S. Appl. No. 15/636,000, Non Final Office Action dated Apr. 29, 2021", 16 pgs.
"U.S. Appl. No. 15/636,000, Response filed Feb. 8, 2021 to Final Office Action dated Aug. 7, 2020", 12 pgs.

* cited by examiner

FIG. 10

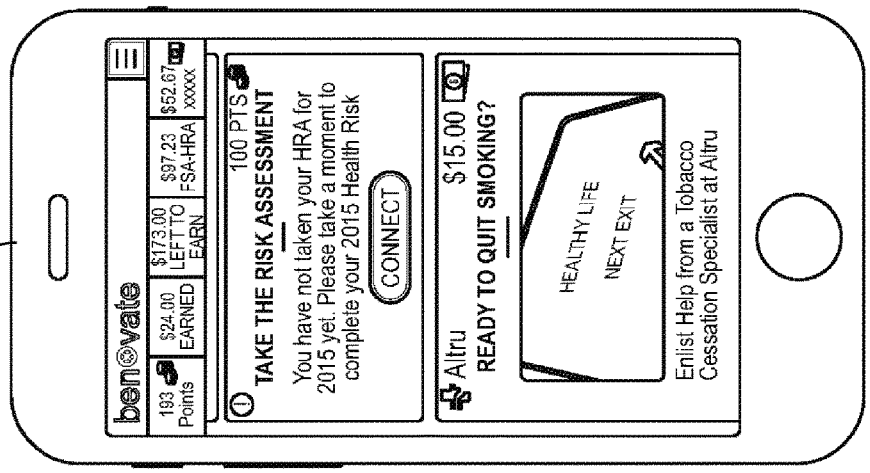
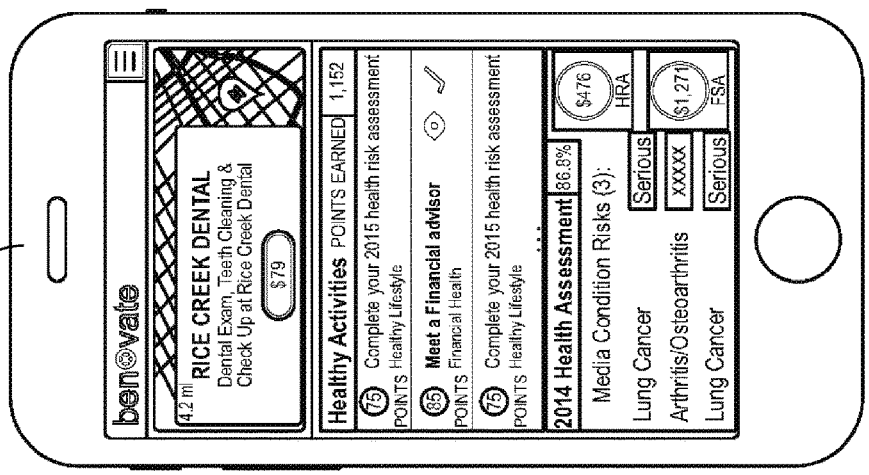
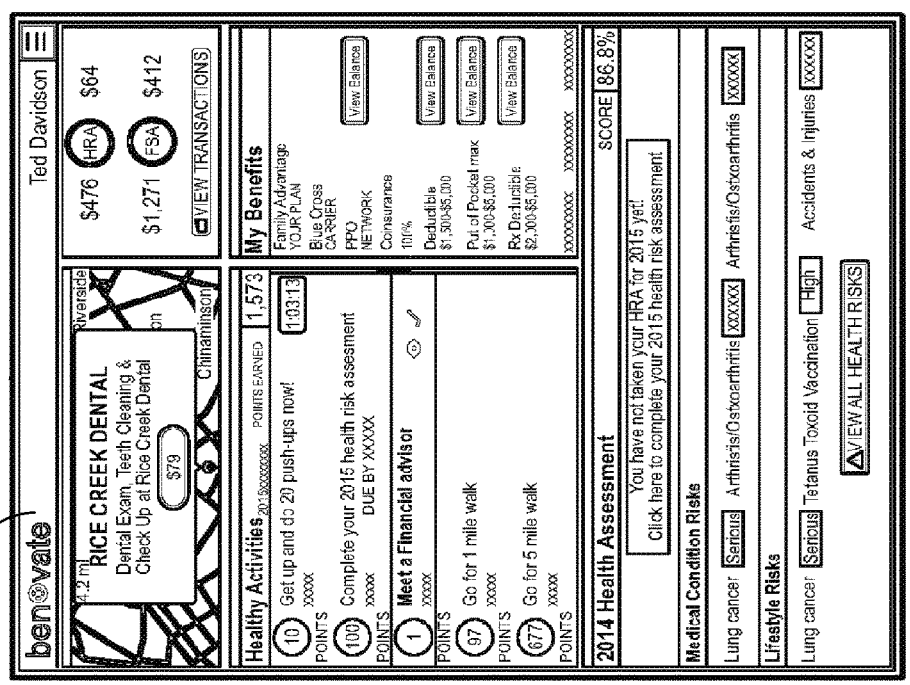
FIG. 11

SYSTEMS AND METHODS FOR DATA CATEGORIZATION AND DELIVERY

CLAIM OF PRIORITY

This patent application is a continuation-in-part of U.S. patent application Ser. No. 13/906,760, entitled "Systems and Methods for Producing Personalized Health Recommendation Data," filed on May 31, 2013, to Mike Reier, which application is a continuation application of U.S. patent application Ser. No. 13/831,294, entitled "Systems and Methods for Producing Personalized Health Recommendation Data," filed on Mar. 14, 2013, to Mike Reier, which claims the benefit of U.S. Provisional Patent Application Ser. No. 61/670,714, entitled "Benovate," filed on Jul. 12, 2012, to Mike Reier, the applications of which are hereby incorporated by reference herein in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Benovate, All Rights Reserved.

BACKGROUND

Information systems provide centralized repositories for data collection. Many information systems provide trigger-based outputs, where each data point is stored and a particular input data point causes a single output. Each output is derived on an existing body of knowledge implemented in the information system, where the existing body of knowledge includes generalizations about the overall population of historical data. Many information systems also include a complex interface that require skilled operators to view, manipulate, or output collected data. What is needed is an improved information system with a simplified interface for collected data.

BRIEF DESCRIPTION OF THE DRAWINGS

FIG. 10 shows a prioritized desktop computer user interface for categorized data according to some examples of the present disclosure.

FIG. 11 shows a prioritized mobile device user interface for categorized data according to some examples of the present disclosure.

Figure 1:
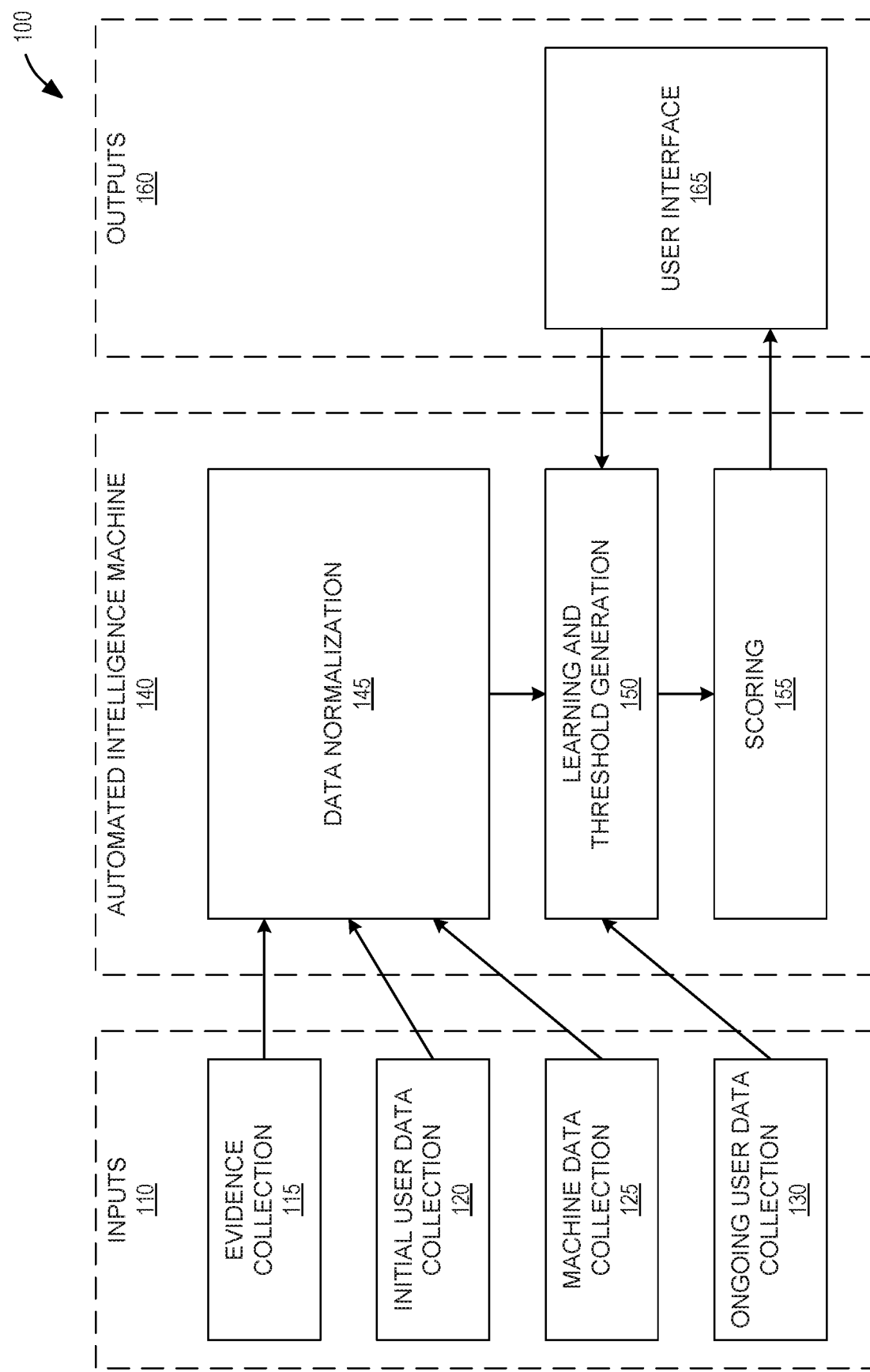
FIG. 1 shows a block diagram of an improved information system according to some examples of the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Disclosed in some examples are systems, methods, and machine-readable media for improved information systems. To address the problems of current information systems, these improved information systems provide a technical solution that includes a predictive learning system and improved data analysis. The data analysis processes multiple data input streams simultaneously, and applies digital signal processing to identify correlation between or among multiple data input streams. The analysis is further personalized based on the input data source. In some examples, inputs include personalized data profile characteristics, including user preferences, user lifestyle risks, and motivational factors. The user interface is used to present outputs according to personalized data profile characteristics. In some examples, the user interface includes multiple graphical information cards that are formatted and prioritized based on relevance or urgency.

FIG. 1 shows a block diagram of an improved information system 100 according to some examples of the present disclosure. The improved information system 100 may be grouped into inputs 110, an automated intelligence machine 140, and outputs 160. The inputs may include an evidence collection module 115, an initial user data collection module 120, a machine data collection module 125, and an ongoing user data collection module 130. The evidence collection module 115 may include scientific data, research paper data, or other empirical or theoretical data. The evidence collection module 115 may receive multiple data sources, and may apply meta-analysis to combine results from the multiple data sources. This meta-analysis may be used to improve the predictive ability of the data sources or reduce the effect of conflicting data. In a healthcare example, this may include combining multiple research papers to determine a recommended number of minutes of exercise per week. The initial user data collection module 120 may collect an initial set of data from a user, such as location information, survey answers, biometric baseline data, or other user information. The machine data collection module 125 may collect data from various databases or other machine-readable media. In a healthcare example, the machine data collection module 125 may collect medical records or receiving a current procedural terminology (CPT) code indicating a particular hospital procedure. The ongoing user data collection module 130 may collect data from a user. This data may include data collected by the initial user data collection module 120, such as location information or new biometric data points.

The data normalization module 145 may receive data from the evidence collection module 115, from the initial user data collection module 120, and from the machine data collection module 125. The data normalization module 145 processes the collected data into normalized data, where the normalized data is formatted in a manner that it can be compared to other normalized data. Normalization may be performed with respect to a static threshold, or may be based on varying personalized thresholds, such as a changing risk as described below with respect to FIG. 4. The data normalization module 145 may also categorize collected or normalized data, where the categorization may include associating data tags as described below with respect to FIGS. 2-3.

The learning and threshold generation module 150 compare normalized data to provide an overall user data analysis. The overall analysis may include identifying or updating thresholds for assigning user tags, such as described below with respect to FIG. 5. In a healthcare example, meta-analysis may determine a threshold number of minutes of exercise per week to maintain a healthy weight, and a series of user data points regarding minutes walked and current weight may change the threshold number of minutes of exercise recommended for that user. The overall analysis may include identifying anomalous events or cross-correlations between data sets, such as described below with respect to FIG. 2. For example, a purchase history may be correlated with a user activity, and a causal relationship may be established between a particular purchase and that user activity. The learning and threshold generation module 150 provides continuous updates to the improved information system 100, and may be used to update the data inputs 110, the data normalization module 145, the learning and threshold generation module 150 itself, the scoring module 155, or the user interface 165. The learning and threshold generation module 150 also receives data from the ongoing user data collection module 130, and is used to update the data analysis and threshold determination.

The scoring module 155 receives analyzed data from the data normalization module 145 and the learning and threshold generation module 150, and generates content for the user interface 165. The content generation may include generation of multiple information cards for a single user that are formatted and prioritized based on relevance or urgency. The user interface 165 may target a user's individual needs and goals immediately. For example, a data point from the ongoing user data collection module 130 may indicate that a user is falling below a desired threshold, and a score or card may be generated to reward the user for activities that may bring the user above the desired threshold. The user interface 165 may provide a dynamically generated graphical user interface, such as described below with respect to FIGS. 10-11. The user interface 165 may also provide a portal for a user or administrator to view or manipulate data within the automated intelligence machine 140. For example, an administrator may adjust a threshold or implement a new data analysis tool within the learning and threshold generation module 145.

Figure 2:
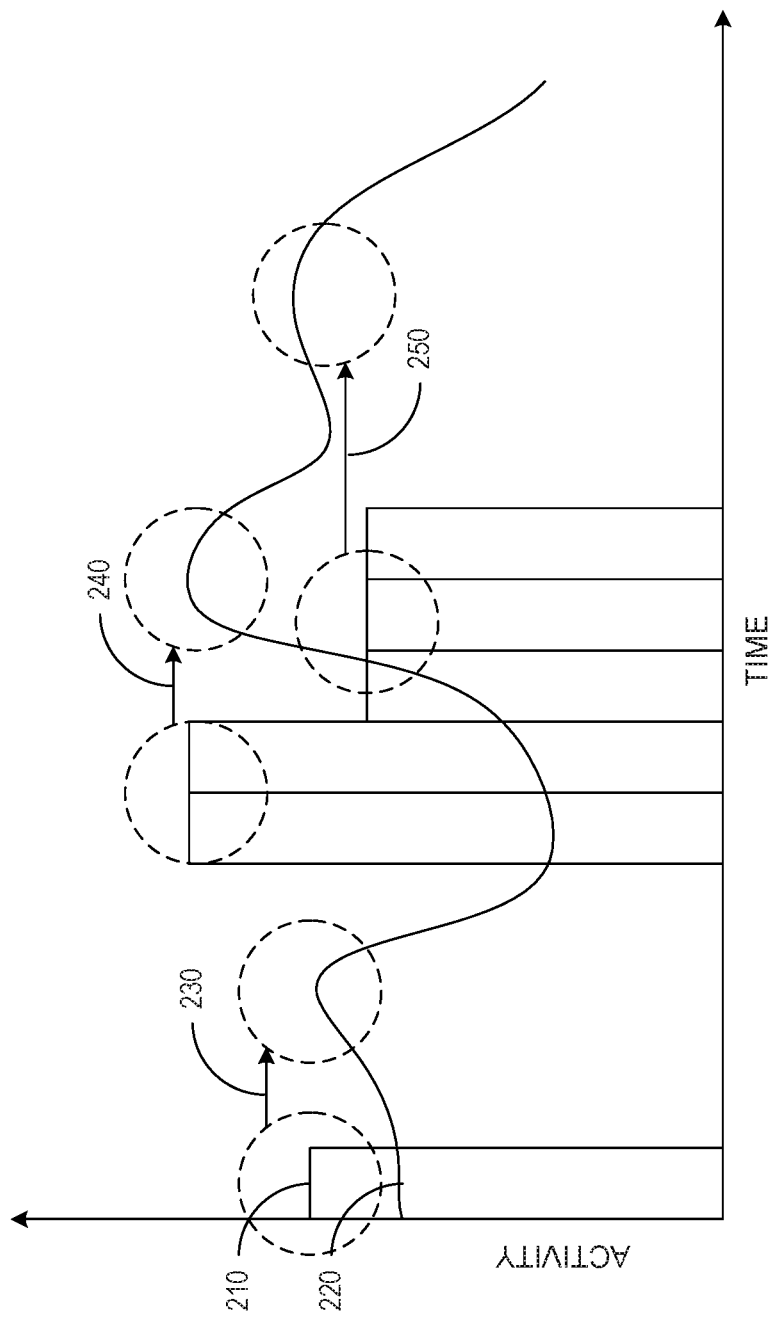
FIG. 2 shows a graph of an event cross-correlation according to some examples of the present disclosure.

FIG. 2 shows a graph of an event cross-correlation 200 according to some examples of the present disclosure. Event cross-correlation 200 may be implemented in the learning and threshold generation module 150 or in other modules within the improved information system 100. Event cross-correlation 200 may be used to identify cross-correlations between data sets or identify anomalous events. While some events may occur simultaneously, many events cause time-delayed effects. The event cross-correlation 200 allows for comparing and contrasting event data sets using digital signal processing techniques, where one data set is time-delayed relative to another data set.

In the example shown in FIG. 2, a discrete data set 210 is compared with a continuous data set 220. The discrete data set 210 may be associated with a particular event, such as an amount of money spent on ice cream. The continuous data set 220 may be associated with a daily activity level, such as a combination of heart rate and steps per minute. Event cross-correlation 200 may identify one or more similarities between the discrete data set 210 and the continuous data set 220, such as events 230, 240, and 250. The event cross-correlation 200 may cross-correlate these two data sets and identify, for example, a time lag between purchasing ice cream and increased daily activity. This may be interpreted as a causal effect between the purchase of ice cream and an increase in daily activity due to guilt or due to increased blood sugar levels. This interpretation may be used within the improved information system 100 to provide periodic motivation for ice cream purchases. The periodic motivation data may also be tracked for its cross-correlation with the discrete data set 210 and with the continuous data set 220.

In addition to analysis of cross-correlation between different event data sets, an autocorrelation may be used to detect or predict an event. For example, an event may have an associated data set characteristic, and that characteristic data set may be autocorrelated with a raw data set to identify subsequent occurrences of that event. In a healthcare example, a predetermined biometric heart rhythm may be associated with a heart fibrillation, and the predetermined rhythm may be autocorrelated with a biometric input data stream to identify a heart fibrillation event.

Other digital signal processing and data processing techniques may be used for data analysis. For example, a single anomalous event may be identified as a causal trigger for another single event based on a mean and standard deviation of a time lag between the triggering event and the subsequent event. In a healthcare example, triggering events may include newly identified health risks, new medical data, a move to a new neighborhood, or a current procedural terminology (CPT) code indicating a hospital visit or procedure. Upon detection of an anomalous event, the data may be reviewed automatically or manually to analyze and identify related subsequent events, and a new causal relationship may be identified and used in subsequent data analysis. In another example, machine learning may be used to build and apply a predictive model. In a healthcare machine learning example, the inputs may include a patient event such as a new medical procedure, and the output may include required and optional rehabilitation steps. In the healthcare machine learning example, training data may include collected health data for a large population, the training data may be categorized and model built using the risks and tags as explained below with respect to FIGS. 4-5. A specific example of the use of event cross-correlation 200 to influence behavior is explained below with respect to FIG. 3.

Figure 3:
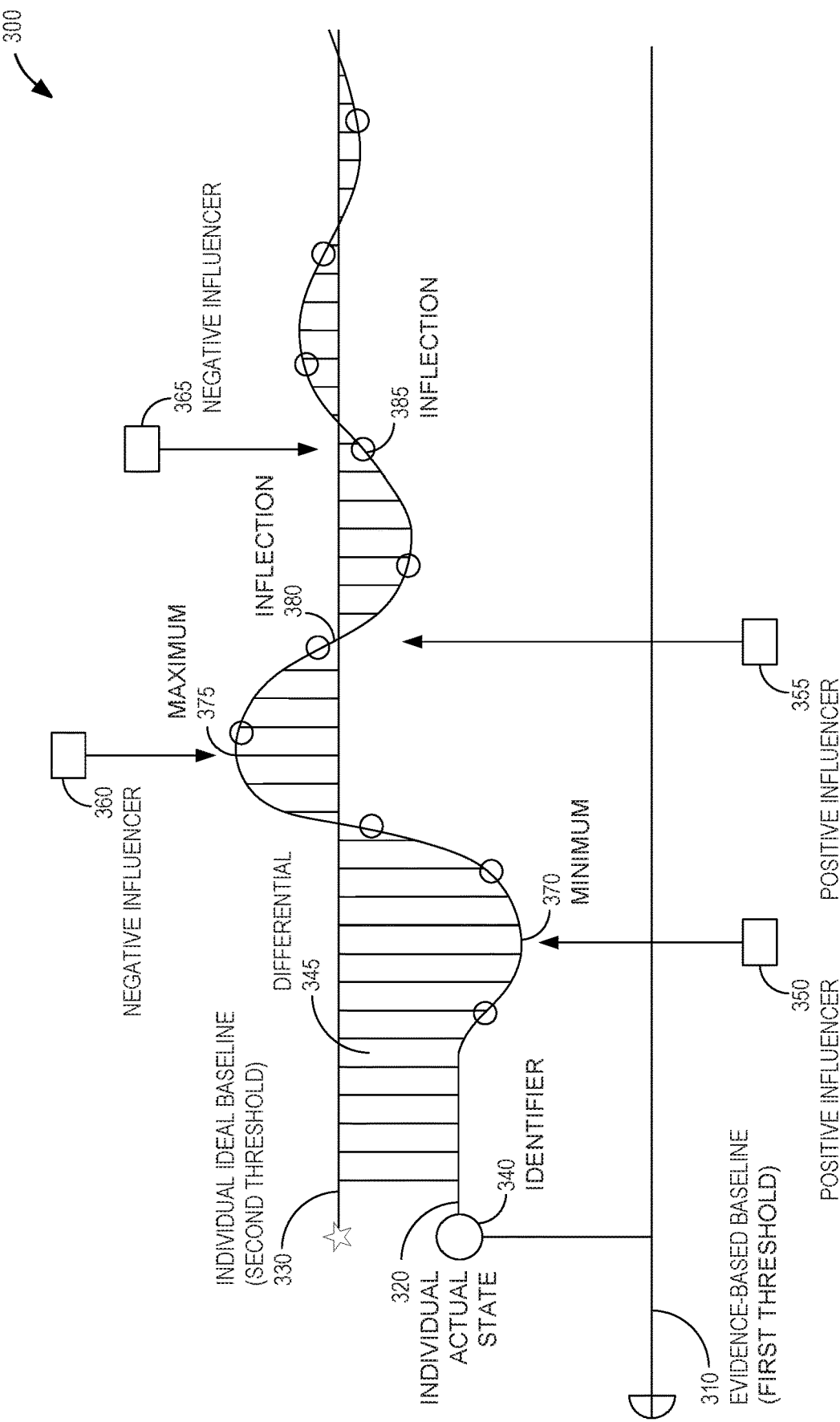
FIG. 3 shows a graph of an individual differential determination according to some examples of the present disclosure.

FIG. 3 shows a graph of an individual differential determination 300 according to some examples of the present disclosure. The determination 300 includes three primary behavior lines: an evidence-based baseline 310, an individual actual state 320, and an individual ideal baseline 330. The evidence-based baseline 310 may be an initial baseline representative of an evidence-based desired level. In a healthcare example, the evidence-based baseline 310 may be a number of hours per sleep or number of steps per day. The value of the evidence-based baseline 310 may be determined through collection of evidenced-based research, actuarial tables, insurance statistics, or organizational standards, such as recommendations from the World Health Organization or from the U.S. Department of Health & Human Services. FIG. 3 shows the evidence-based baseline 310 as a straight line for discussion purposes, though the evidence-based baseline 310 may be revised to be curved or angled based on new evidenced-based information.

The value of the individual ideal baseline 330 may be determined as an offset from the evidence-based baseline 310. In a healthcare example, the evidence-based baseline 310 may determine that people generally should complete 10,000 steps per day, however the individual ideal baseline 330 may indicate that the particular user should complete 15,000 steps per day. The value of the individual ideal baseline 330 may be determined through collection of initial user data collection, such as Health Risk Assessments or surveys. The individual ideal baseline 330 may also be determined through machine data collection, such as underwriting assessments, claims data, actuarial tables, wellness reports, and insurance data. The individual ideal baseline 330 may also be determined through previously gathered real-time data, such as previously gathered GPS tracking data or personal health monitoring device data. FIG. 3 shows the individual ideal baseline 330 as a straight line for discussion purposes, though the individual ideal baseline 330 may be revised to be curved or angled based on new individual-specific information.

The user may be assigned one or more groups (e.g., tags). In a healthcare example, a tag may include an increased risk of diabetes. The tags may be applied by categorization system (e.g., tagging system) as explained below with respect to FIGS. 4-5. The individual ideal baseline 330 may be determined using information specific to a single user, using information specific to a tagged group to which the user belongs, or both. Tags may also be used in various combinations due to how each tag affects other tags, such as in the comorbidity of two or more tags. In a healthcare example, an increased risk of obesity is associated with an increased risk of diabetes. The categorization system may alter the individual ideal baseline 330 using data gathered from additional health risks, co-morbidities, stress factors, lifestyle factors, demographic data sets, geographic data sets, or alternate industry relevancy.

The value of the individual actual state 320 may be determined relative to the evidence-based baseline 310 or relative to the individual ideal baseline 330. An identifier 340 may be used as an initial data point to determine the initial level of the individual actual state 320. The difference between the individual actual state 320 and the individual ideal baseline 330 may be referred to as the differential 345, where the differential 345 may be used to represent the degree to which a user is below or above the individual ideal baseline 330. In a healthcare example, a user cholesterol level may be below or above a desired level. Following the initial identifier 370, subsequent identifier data points may be collected from the user, such as via user surveys, medical reports, wearable technology, or other data sources. The individual actual state 320 may be depicted as a curved line that fits the multiple data points, such as using an n-th order polynomial. The differential 345 may be determined as the area under or above the curved individual actual state 320.

The individual ideal baseline 330 may represent an improved or optimized level for a user. The closer a user gets to individual ideal baseline 330, the smaller the differential 345 area will be. Various events or actions may alter a user's current individual actual state 320, and may result in a reduction of the differential 345. These events or actions may be referred to as positive or negative influencers. For example, a positive influencer 350 may occur during a decreasing portion of the individual actual state 320, and may cause the individual actual state 320 to move positively toward the individual ideal baseline 330. Similarly, a negative influencer 360 may occur during an increasing portion of the individual actual state 320, and may cause the individual actual state 320 to move negatively toward the individual ideal baseline 330. In a healthcare example, the positive influencer 350 may be an e-mail encouraging a user to increase a number of hours of sleep per night, and a negative influencer 360 may be an e-mail encouraging a user to decrease a number of hours of sleep per night. The positive influencer 350 or negative influencer 360 may occur on a local minimum 370 or local maximum 375. In the healthcare sleeping example, an e-mail that is received following the shortest night of sleep may result in an immediate improvement in sleep. Other influencers may occur at or near an inflection point on the individual actual state 320. These points of inflection occur on the individual actual state 320 where the curve changes between being concave downward and being concave upward. As shown in FIG. 3, positive influencer 355 occurs near inflection point 380, and negative influencer 365 occurs near inflection point 385. In an example, the inflection point influencer may be an action or event that is designed to change the rate (e.g., first derivative of the curve) at which a value is changing. In a healthcare example, a user may be decreasing a bodyweight measurement by two pounds per month, and the positive influencer 355 may be used to change that trend at the inflection point 380 to increase bodyweight measurement by one half pound per month. Multiple influencers may be used at various times to reduce the differential 345 area over time, such as shown in FIG. 3. The particular use of tags to generate baselines or influencers are explained below with respect to FIGS. 4-9.

Figure 4:
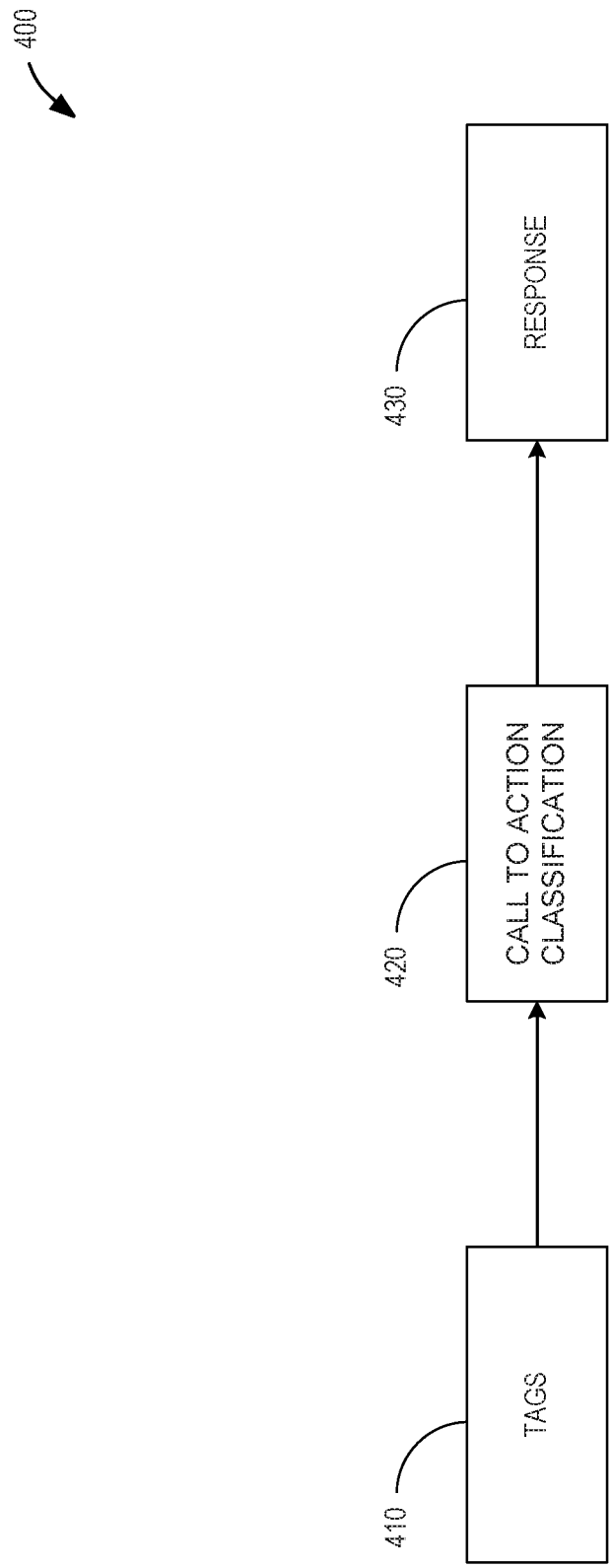
FIG. 4 shows a flowchart of a method for data categorization according to some examples of the present disclosure.

FIG. 4 shows a flowchart of a method 400 for data categorization according to some examples of the present disclosure. Method 400 may be implemented in one or more modules with the improved information system 100. Method 400 may include a tag assignment module 410, call to action classification module 420, and a response module 430. The tag assignment module 410 may provide an initial categorization of normalized data. The tagging categorization module may assign tag categories based on various factors, where the factors may include information generated via analysis of data sets or risk scores. These factors may be compared to bodies of evidence that indicate what is the best practice for the needs of the specific individual. Tagging categorization factors may also include environmental factors, such as availability of resources in the local community, cost and quality of services, or access to care or proximity to healthy choices. For example, data may include survey answers, biometric data, or purchases, and the data may be tagged (e.g., categorized). For example, a combination of purchases and biometric data may be associated with an activity level tag, or a combination of survey answers and purchases may be associated with a financial activity level tag.

The call to action classification module 420 may receive data and assigned tags, and may categorize the data and assigned tags into call to action categories that require a user action. In an example, a purchase history and survey answers may indicate a product may be reaching the end of a safe usage lifetime, and a call to action category may include a suggested product replacement or recall. In another example, biometric data may be combined with medical history data to generate a call to action category of a high risk for stroke or heart attack. The response module 430 combines data, tags, and call to action classification to generate, prioritize, and categorize recommended user responses. The response module 430 may include providing motivation for addressing each call to action category, such as providing a rebate for a suggested product replacement. The response module 430 may also aggregate data, tags, and call to action classification over a number of users within a user group, and may provide recommended updates to organization policies.

Figure 5:
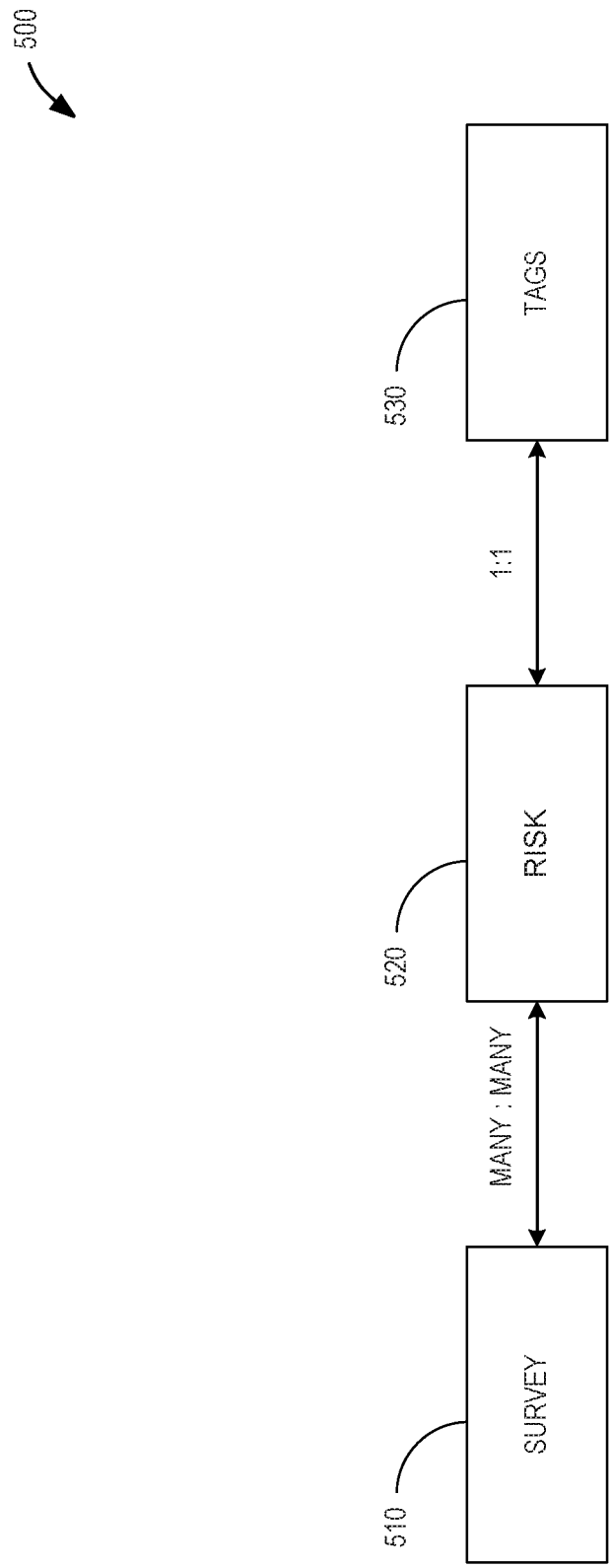
FIG. 5 shows a block diagram of tag mapping according to some examples of the present disclosure.

FIG. 5 shows a block diagram of tag mapping 500 according to some examples of the present disclosure. Tag mapping 500 shows an example configuration of the relationship between surveys 510, risks 520, and tags 530. Surveys 510 may be used to provide data that is assigned to various risks 520. In an example, the relationship between surveys 510 and risks 520 may be described as a many-to-many relationship, where a single survey question may be associated with one or more risks, or where a single risk may be associated with one or more survey questions. Though tag mapping 500 shows risks 520 as related to surveys 510, other data may be used to determine risks 520.

Surveys 510 are an example method of data collection. In an example, surveys 510 collect biographical information about the user, where the user may enter biographical information during a survey, or a survey may retrieve stored biographical information to help interpret or generate other survey questions. The surveys 510 may include binary responses or multiple-answer responses. The survey questions may be organized into serial groups, nested groups, or hierarchical groups. The survey questions may be organized and presented based on various factors, such as priority or level of invasiveness. For example, priority may be determined based on which question is the most important, or may be organized to ask easier questions before more difficult questions. The level of invasiveness may be used to compare the invasiveness of a question with a particular user's wiliness or ability to answer a question. The level of invasiveness may be compared to a question readiness threshold associated with a user, where the user is only asked questions that do not exceed the user's question readiness threshold. For example, a user may respond to several medical survey questions with "prefer not to respond," and the remainder of the survey may avoid medical survey questions.

Each survey answer may increment a number of points associated with a particular risk 520. In an example, survey answers may be grouped and assign points according to a table. An example table is shown below:

TABLE 1

Carbon Monoxide Awareness Question Table

| Questions: | Points: |
|---|---|
| Do you have carbon monoxide detectors in your home? | 9 |
| Do you check your detectors on a monthly basis? | 5 |
| Does your family have an exit plan in the case of an emergency? | 5 |
| Threshold: | 8 |

As shown in Table 1, an answer to the first question may be assigned 9 points, which may exceed the threshold of 8 points. Other combinations of questions and points may be used.

A single survey question may result in identification of multiple risk categories. Conversely, a single risk may result in generation or prompting of multiple additional survey questions. Risks 520 may include multiple risk subfactors, and a survey 510 that triggers any subfactor may result in assignment of the risk 520. In a healthcare example, confirming smoking may result in assigning various point values for depression risk, lung disease risk, and heart disease risk. Risks 520 may have an associated value and adjustable threshold, and a risk 520 may be associated when the associated value exceeds the adjustable threshold. Risks 520 may also have an adjustable hysteresis with associated adjustable minimum and maximum thresholds, where the risk 520 is associated when the value exceeds the maximum threshold, and where the risk 520 is disassociated when the value falls below the minimum threshold. A survey question may also result in negative points, thereby reducing the likelihood of assigning a particular risk 520.

In an example, the relationship between risks 520 and tags 530 may be described as a one-to-one relationship, though other relationships configurations may be used. For example, each risk 520 may generate a specific tag 530. Risk categories may be generated or derived from user data or from third-party data sets. Tags 530 may have an associated value and adjustable threshold, and a tag 530 may be associated when the associated value exceeds the adjustable threshold. Tags 530 may also have an adjustable hysteresis with associated adjustable minimum and maximum thresholds, where the tag 530 is associated when the value exceeds the maximum threshold, and where the tag 530 is disassociated when the value falls below the minimum threshold. Tags 530 may include multiple tag subfactors, and a risk 520 that triggers any tag subfactor may result in assignment of the tag 530. In a healthcare example, any one of multiple cardiovascular risks may be compared to a threshold value, and a heart disease tag may be associated when any of the cardiovascular risks exceeds the threshold value. Further, a first tag may be associated with another tag. This association may be referred to as comorbidity. For example, a heart disease tag may be associated with a diabetes tag. Tags 530 may be identified from external data sources, and may be used to generate a risk 520, which in turn may be used to generate one or more surveys 510.

Figure 6:
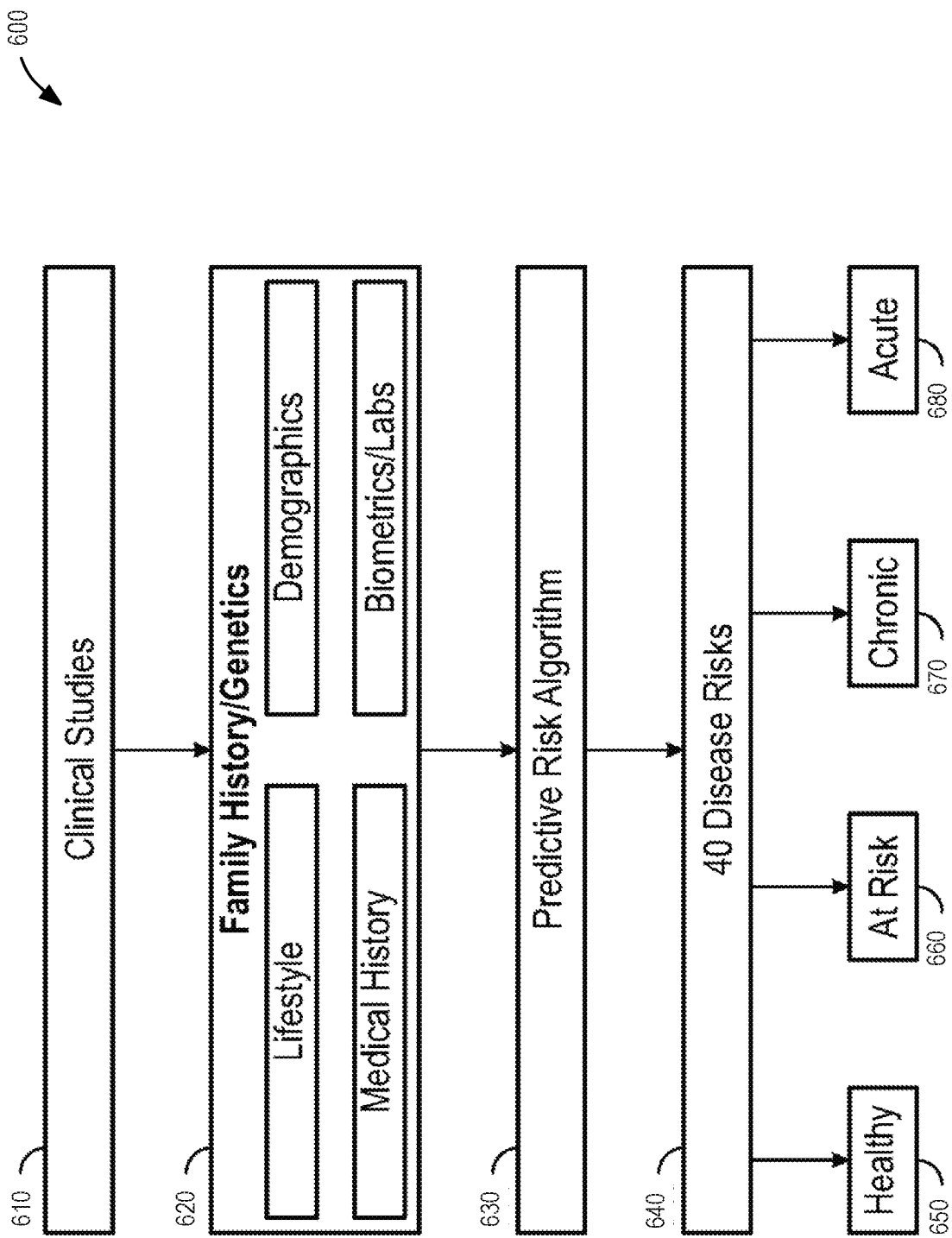
FIG. 6 shows a flowchart of an example method for healthcare data categorization according to some examples of the present disclosure.

FIG. 6 shows a system architecture diagram 600 according to some examples of the present disclosure. The system architecture diagram 600 includes various modules described above. For example, data collection 110 in FIG. 1 may be decomposed into generalized clinical study data 610 and into personalized data 620, and the risks and tags described in FIGS. 4-5 may be captured in the risk mapping 640 as described below. Personalized data 620 may include lifestyle data, medical history data, family history and genetic data, demographic data, or biometric or laboratory results data. The study data 610 and into personalized data 620 may be fed into a predictive risk algorithm 630, such as using the tag mapping 500 described above. The predictive risk algorithm 630 may be used to determine disease risks 640, such as by mapping tags to various diseases or disease categories. The disease risks 640 may be allocated into various adjusted diagnosis groups (ADGs), such as a healthy group 650, an at-risk group 660, a chronic group 670, or an acute group 680. Disease risks 640 may be placed in ADGs based on a number of clinical dimensions. Clinical dimensions may include duration (e.g., acute, recurrent, or chronic), severity (e.g., minor, major, stable, unstable), diagnostic certainty (e.g., symptoms versus diseases), etiology (e.g., infectious, injury-caused), or specialty care (e.g., medical, surgical, obstetric, hematology).

Figure 7:
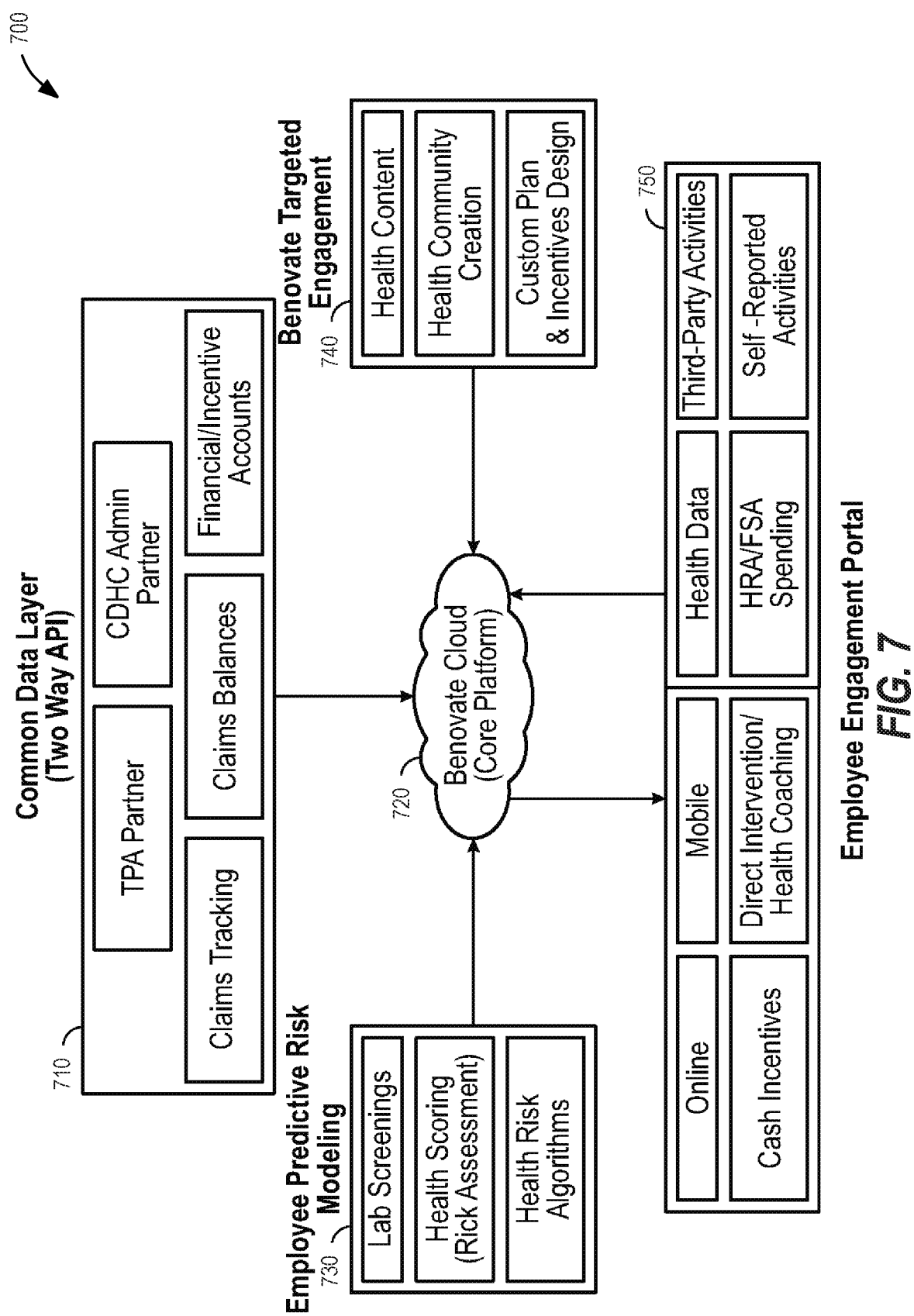
FIG. 7 shows a block diagram of an information system according to some examples of the present disclosure.

FIG. 7 shows a block diagram of an information system 700 according to some examples of the present disclosure. The information system 700 includes various modules described above, such as those described within the improved information system 100. For example, the mapping of survey questions, events, risks, and tags described in FIGS. 1-5 may be included within the predictive risk modeling module 730, or data gathering 110 may include data provided by the common data layer 710, by the targeted engagement module 740, or by the engagement portal module 750. The information system 700 includes a common data layer 710. The common data layer 710 may be implemented as a two-way application program interface (API) that enables various data sources to manipulate and transfer data. In a healthcare example, the common data layer 710 may include a third-party administrator (TPA) partner module, a consumer-driven health care (CDHC) administrative partner module, a claims tracking module, a claims balancing module, or financial or incentive account module. The common data layer 710 may manipulate and provide data to a core platform 720. The core platform 720 may also exchange data with one or more of a predictive risk modeling module 730, a targeted engagement module 740, or an engagement portal module 750. The predictive risk modeling module 730 may include gathering data from lab screenings, data from health scoring, or data from health risk algorithms. The targeted engagement module 740 may include gathering data from health content, health community creation, or custom plan and incentive designs. The engagement portal module 750 may include various user interfaces, such as online interfaces, mobile electronic device interfaces, cash incentive interfaces, or interfaces via direct intervention or health coaching. The engagement portal module 750 may also include gathering data from user health data sources, from third party activities, from health reimbursement account (HRA) or flexible spending account (FSA) spending, and from self-reported activities. The collected data may be used to generate risks 520, tags 530, or recommended responses 400 as described above. The engagement portal module 750 is described below with respect to FIGS. 8-11.

Figure 8:
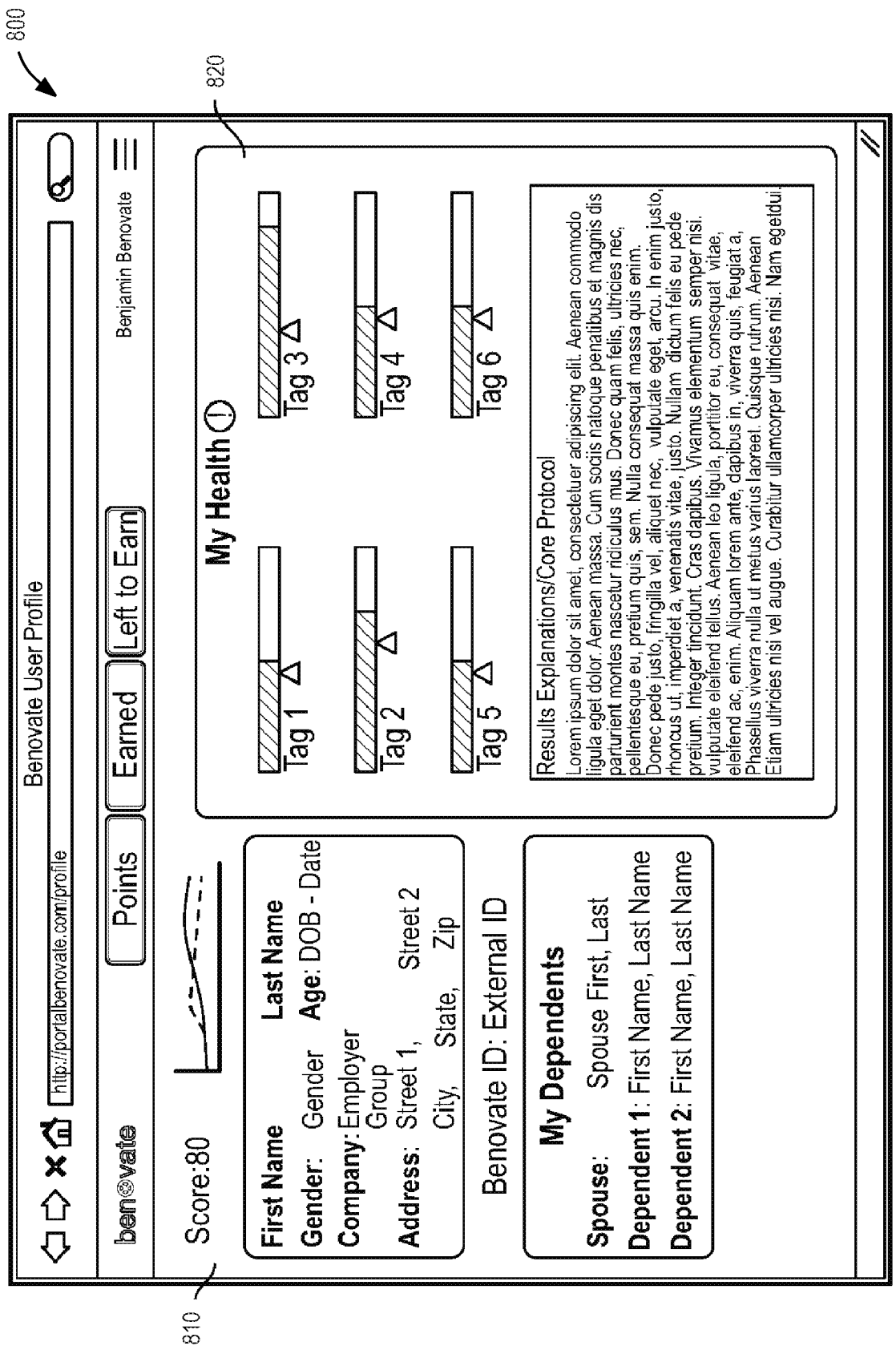
FIG. 8 shows a first user interface for categorized healthcare data according to some examples of the present disclosure.

FIG. 8 shows a first user interface 800 for categorized data according to some examples of the present disclosure. The first user interface 800 is a healthcare example of the user interface 165 described above. The first user interface 800 may include a user information summary 810 and a user health tag summary 820. The user information summary 810 may include an overall score with sparkline (e.g., simplified) graph of the score over time. The user information summary 810 may also include user demographic information or user family information. The user health tag summary 820 may include a progress bar for each tag, where the progress bar shows a user's status for that tag relative to a triangular goal value. Additional detail for the user information summary 810 is described relative to FIG. 9.

Figure 9:
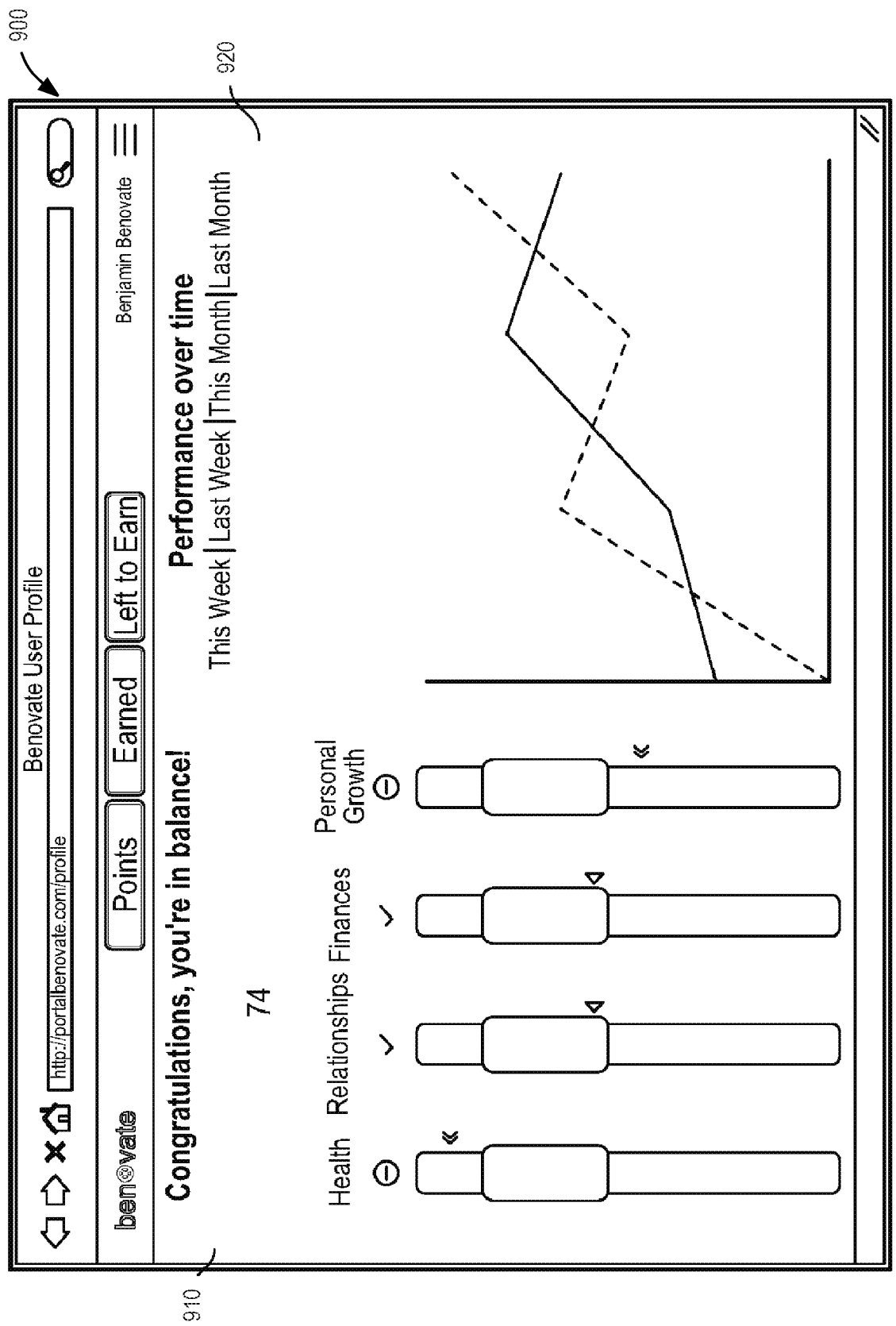
FIG. 9 shows a second user interface for categorized data according to some examples of the present disclosure.

FIG. 9 shows a second user interface 900 for categorized data according to some examples of the present disclosure. The second user interface 900 is also a healthcare example of the user interface 165 described above. The second user interface 900 includes a detailed category score 910 and a performance trend line 920. The detailed category score 910 may be divided into multiple categories (e.g., pillars). The detailed category score 910 and performance trend line 920 may be used as an aggregate data portal, where the scores represent a combination of a user's actions relative to risk, tags, and surveys as described with respect to FIGS. 1-5. For example, the categories allow a user to view a small number of easily understood scores, thereby preventing the need for the user to review the large amounts of data within the information system. In a financial maintenance example, a user may have answered financial survey questions and completed a review of his or her portfolio, and a financial category with the detailed category score 910 may display a checkmark to indicate the user is performing an appropriate level of financial maintenance.

The detailed category score 910 may include multiple categories, such as physical health, relationships, financial health, and personal growth. The physical health category may include exercise, nutrition, health management, pharmacy, mental health, and treatment. The relationships category may include relationships with parents, relationships with siblings, relationships with a spouse or partner, relationships with children and dependent family members, and relationships with the relevant community. The financial health category may include having enough money, saving enough money, retirement, and legacy financial stability. The personal growth category may include personal growth, professional growth, coworker growth, and community growth. These categories may be used to focus on maintaining an appropriate balance. The categories may be organized or presented to facilitate ongoing engagement in the information system. The categories may be used to analyze date across multiple segments or behaviors.

Each category within the detailed category score 910 may show a score and range relative to the category. The score and range may be defined to increase the likelihood that a user will improve or maintain that category without exceeding or underperforming in that category. The score may be calculated as a deviation from the desired level. For example, the score may be calculated as the statistical standard deviation from the desired level, or may be calculated as the difference between the user level and a predetermined category standard deviation.

The desired level may be set to a particular level to encourage participation while maintaining balance, and may be referred to as optimum moderation. In an example, the desired level may be set to eighty, where values below eighty indicate a category deficit and values above eighty indicate a category imbalance. The desired level may be set system-wide, or may be an adjustable value that is tailored to the patterns and motivations of an individual.

The overall score may be generated as a weighted average of the individual category scores, where the individual category scores are weighted according to that category's importance to the overall health picture. The presentation of the individual categories within the detailed category score 910 is organized to visually depict the balance that the user should strike between the various categories. The individual categories may have associated recommendations of specific tasks to improve or rebalance the scores, where the associated recommendations may be indicated on the detailed category score 910 or may be accessed by clicking on one of the categories. The scores and recommendations associated with each category may be updated throughout each day. The scores may be grouped into time periods. For example, the score may represent the current week's progress relative to a goal, allowing a user to implement recommendations to improve the score within the week.

The individual category scores may be modified by various mechanisms. As described above, a score may be improved by completing a recommendation. A score may also be drained slowly over time to encourage participating in the recommended activities. A score may be transferrable. For example, individuals may be associated with a group, and individuals within that group may be allowed to donate or share points toward a score. A score may also be lockable due to inactivity or other causes. For example, a score may be locked, and a user may be required to complete a recommended task before unlocking access to the score.

The performance trend line 920 may be used to provide a simplified display of a user's performance values over time. The performance values shown in the performance trend line 920 may include a single category score, an overall score, or a combination of other scores or input data.

Figure 10:
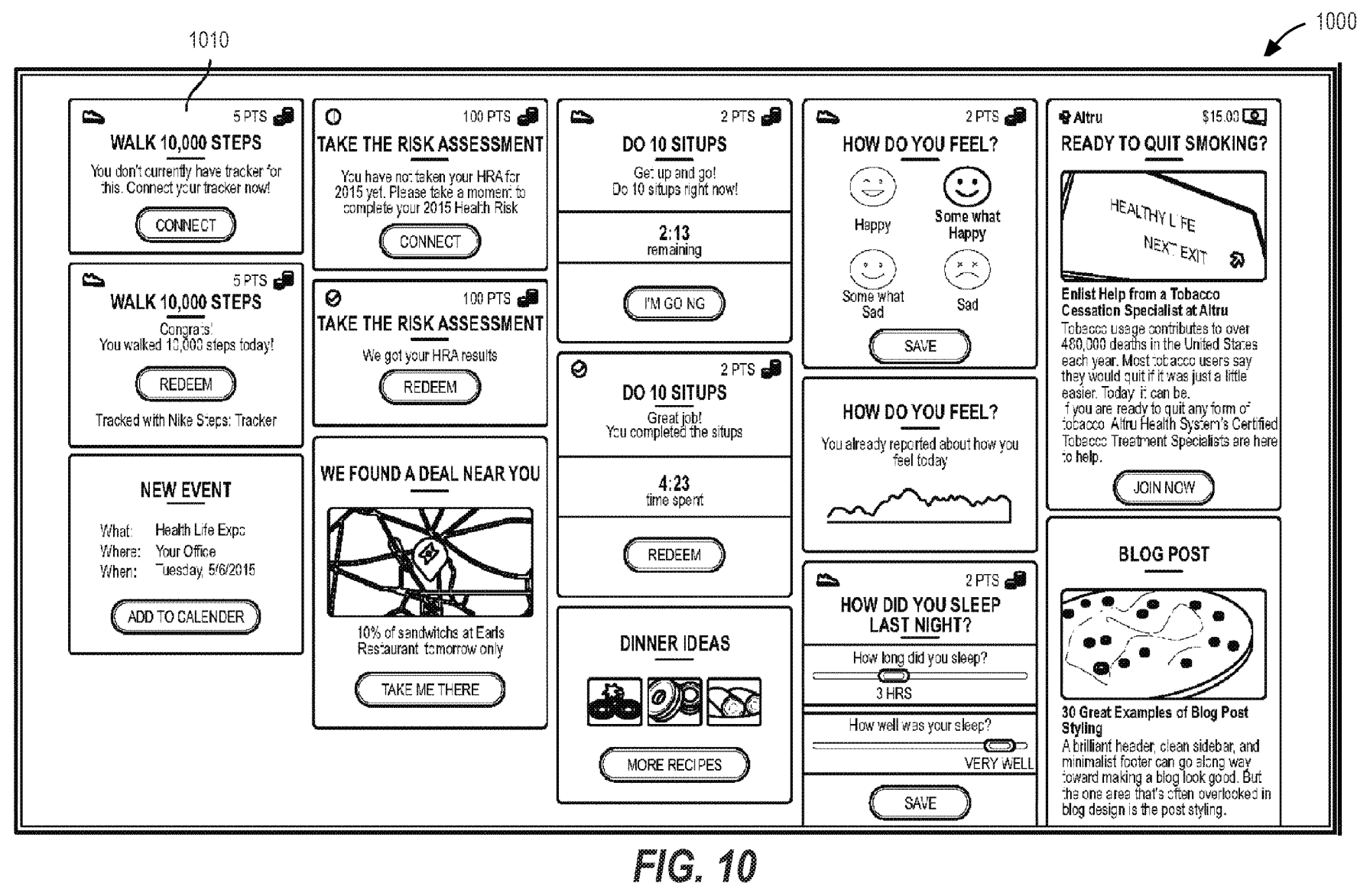

FIG. 10 shows a prioritized desktop computer graphical user interface 1000 for categorized data according to some examples of the present disclosure. The prioritized desktop graphical computer user interface 1000 may provide a series of cards 1010. The cards 1010 may include various care protocols, assessments, rewards, disease indicators, surveys, assessments, location information, exercise instruction, nutrition suggestions, health or well-being assessments, and other recommendations or information. Each card may include one or more interactive features, such as buttons, maps, graphs, or GUI-based surveys. For example, a user may press a card button to schedule an appointment at a suggested time, may press a card button to activate another application, or may click an emoticon or slide a sliding bar to respond to a survey.

The cards 1010 may be organized and presented based on various factors, such as priority or level of invasiveness. For example, priority may be determined based on which card question is the most useful in determining a particular user attribute or status, or may be organized to provide more engaging or entertaining cards above more difficult cards. The level of invasiveness may be used to compare the invasiveness of a card with a particular user's wiliness or ability to undertake an action. The level of invasiveness may be compared to a card readiness threshold associated with a user, where the user is only presented with cards that do not exceed the user's card readiness threshold. For example, a user may dismiss several dental cards, and subsequent dental cards may not be presented to the user for several days. Similarly, a card may be delayed by a time period that is predetermined or set by the user, and the delay may be used to adjust the level of invasiveness associated with the user.

Each card may have an associated point value. The point values may be used to provide motivation to participate in the stated card activity. The point values may also be used by the improved information system 100, such as in assigning tags, risks, or scores. The point values may be used to determine direct rewards, such as within an HSA account, FSA account, or deductible credit account. The points or reward values may be modified dynamically for each user, such as being modified based on how a user responds to positive feedback. The point values may also be used to organize the cards, or the card organization may be used to reallocate the position of the cards. For example, a higher point value may be associated with a task with a higher level of invasiveness, thereby encouraging the user to participate in that activity.

FIG. 11 shows a prioritized mobile device user interface 1100 for categorized data according to some examples of the present disclosure. The prioritized mobile device user interface 1100 may include a tablet interface 1110, a first phone interface 1120, or a second phone interface 1130. The prioritized mobile device user interface 1100 offers features of the prioritized desktop computer user interface 1000, but also offers features particular to mobile electronic devices. For example, the tablet interface 1110 may include the ability to provide and display a user location in addition to multiple cards.

The user location may be used to generate or prioritize cards. A database of locations relevant to the user may be stored locally or remotely, and the user location may be compared against the location database to generate or prioritize cards. Cards may be generated or prioritized based on proximity. For example, cards associated with activities near the user may have a higher associated priority. In a healthcare example, activities hear the user may include discounts for healthy restaurants or grocery stores or suggested outdoor physical activity locations. The database may include user preferences for types of service providers or product vendors, and cards may be generated or prioritized based on a combination of user preference and proximity. In a healthcare example, a user may indicate a preference for a particular healthcare provider or healthcare network, and a card may be generated for the nearest two in-network healthcare providers. The location may be used in combination with a database maintained by a service providers or product vendors to generate or prioritize cards. For example, a service provider may maintain a schedule of appointments, and a card may be generated based on a nearby appointment availability. Similarly, a product vendor may maintain an inventory of products, and a card may be generated based on the availability of a product that can be used to address a user's identified risk or tag. As the user's mobile electronic device is moved, the user cards may be reexamined for relevance or rearranged based on priority or proximity. A user location may also be sent to a service provider or product vendor. In a healthcare example, anonymous details about a user risks and a user proximity may be sent to a healthcare provider. In a product vendor example, anonymous details may be sent about a user's product preferences and user location may be sent to a nearby store location. In some examples, discounts offered within cards may be funded by the service provider, by the user's health plan, or by another entity. The user location may also be used to participate or automatically track activities. In a healthcare example, a card activity may include traveling to a doctor or going for a walk. The level of automation in reporting may be used to determine point values associated with various cards. For example, a walk tracked via mobile device GPS may have a higher point value than a desktop interface card that uses a button to confirm a walk.

Additional features particular to mobile electronic devices include improved communication and notifications. Various notifications may be sent wirelessly to the mobile device, such as via e-mail, application push notifications, text messaging, or other communication methods. Some cards may be associated with an activity that is time-sensitive, such as a medical intervention. In a healthcare example, a critical event may include a heart fibrillation event, and a mobile device may immediately provide additional diagnostic tools or a video consolation with a heart specialist. Mobile devices may also send information to third-parties for third-party intervention. In a healthcare example, a mobile device may send a biometric heart rhythm to a primary care physician for review, or may trigger a health coach notification when the user is determined to have skipped a health coaching session. Other mobile electronic device features may be used, such as sensors, communication modules, or data connections to peripheral wearable technology. For example, the mobile electronic device may interface with a pedometer to track steps, and may interface with a smart watch to provide time-sensitive card notifications.

Figure 12:
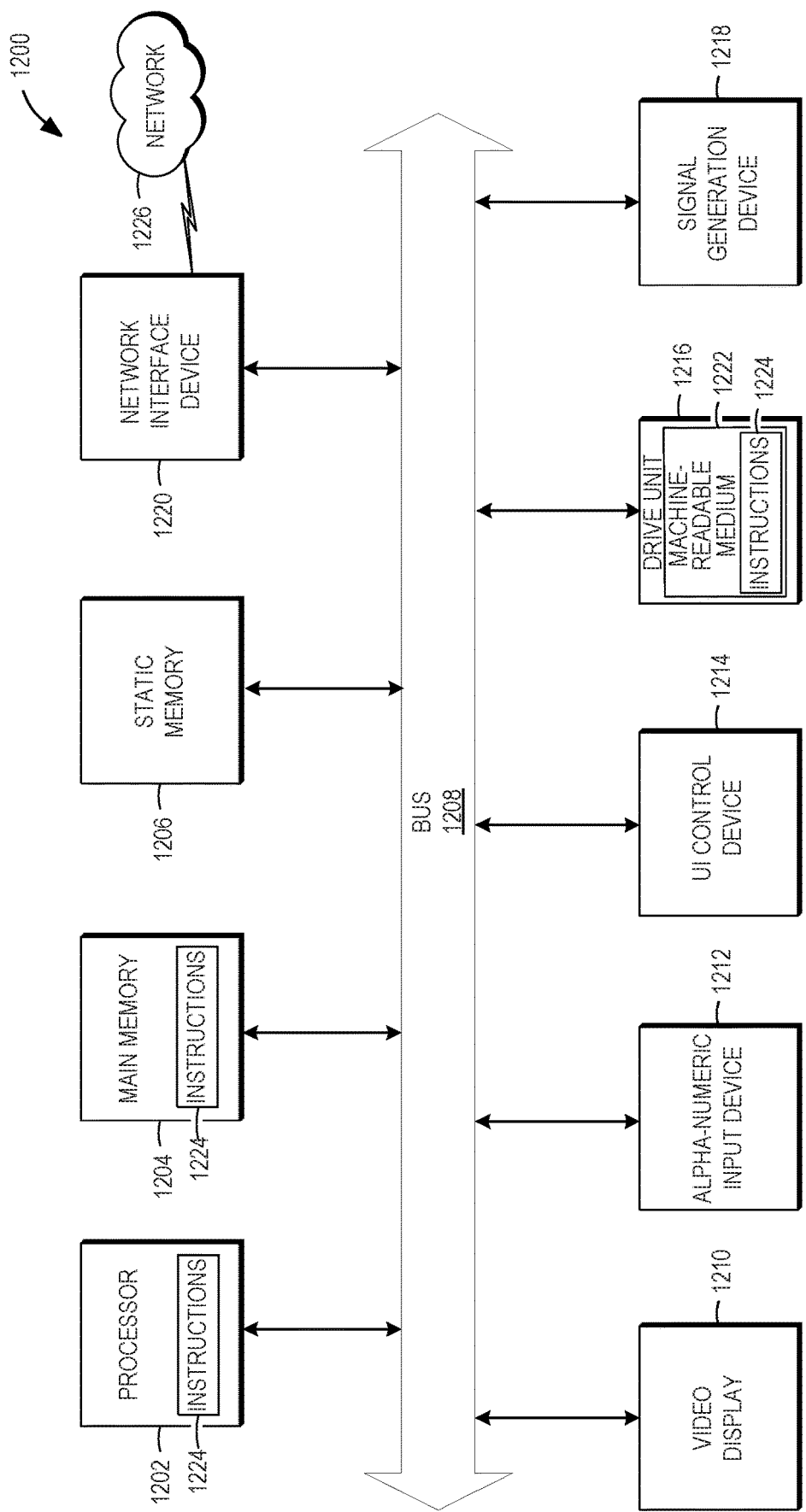
FIG. 12 shows a block diagram of a machine according to some examples of the present disclosure.

FIG. 12 is a block diagram of machine in the example form of a computer system 1200 within which instructions, for causing the machine to perform any one or more of the methodologies discussed herein, may be executed. For example, any one of the components shown in FIG. 1 may be or contain one or more of the components described in FIG. 12. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a notebook PC, a docking station, a wireless access point, a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. The machine may contain components not shown in FIG. 12 or only a subset of the components shown in FIG. 12.

The example computer system 1200 includes a processor 1202 (e.g., a central processing unit (CPU), a graphics processing unit (GPU) or both), a main memory 1204 and a static memory 1206, which communicate with each other via a bus 1208. The computer system 1200 may further include a video display unit 1210 (e.g., a liquid crystal display (LCD) or a cathode ray tube (CRT)). The computer system 1200 also includes an alphanumeric input device 1212 (e.g., a keyboard), a user interface (UI) navigation device 1214 (e.g., a mouse), a disk drive unit 1216, a signal generation device 1218 (e.g., a speaker) and a network interface device 1220.

The disk drive unit 1216 includes a machine-readable medium 1222 on which is stored one or more sets of instructions and data structures (e.g., software) 1224 embodying or used by any one or more of the methodologies or functions described herein. The instructions 1224 may also reside, completely or at least partially, within the main memory 1204, static memory 1206, and/or within the processor 1202 during execution thereof by the computer system 1200, the main memory 1204 and the processor 1202 also constituting machine-readable media.

While the machine-readable medium 1222 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., Erasable Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1224 may further be transmitted or received over a communications network 1226 using a transmission medium. The instructions 1224 may be transmitted using the network interface device 1220 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software. Network interface 1220 may wirelessly transmit data and may include an antenna.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may access the memory device later to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least one or more processors or processor-implemented modules may perform some of the operations of a method. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., APIs).

Example embodiments may be implemented in digital electronic circuitry, in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. FIG. 12 depicts an example hardware (e.g., machine) and software architectures that may be deployed, in various example embodiments.

An example embodiment includes an improved information system.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to limit the scope of this application voluntarily to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for facilitating data categorization and delivery, the method comprising electronic operations performed by at least one computing machine having at least one hardware processor and at least one memory, with the electronic operations comprising:
   receiving an input data set and sensor data associated with a user;
   normalizing the input data set, the input data set including at least one input event;
   comparing the normalized data set to a stored data set, the comparison indicating a relationship between the at least one input event in the normalized data set and at least one stored event in the stored data set;
   generating a plurality of graphical user interface (GUI) output card objects based on the comparison, each of the plurality of GUI output card objects configured for display on a user device, each of the plurality of GUI output card objects having an associated card object priority level;
   determining a first arrangement of the GUI output card objects based on the plurality of GUI output card objects and the received sensor data;
   presenting the plurality of GUI output card objects in the first arrangement within a graphical user interface (GUI) display, the first arrangement based on the plurality of GUI output card objects and the received sensor data;
   receiving a user data set update based on a user interaction with a selected card object of the plurality of GUI output card objects;
   associating a completed status with one of the plurality of GUI output card objects based on the user data set update;
   determining a second arrangement of the GUI output card objects based on the card object priority level associated with each of the plurality of GUI output card objects, the second arrangement excluding the GUI output card object associated with the completed status and including at least one revealed output card object not previously displayed within the first arrangement; and
   presenting the second arrangement within the GUI display.

2. The method of claim 1, wherein the received user data set update is based on a GUI input associated with one of the plurality of GUI input objects.

3. The method of claim 1, wherein the comparing includes cross-correlating the normalized data set with the stored data set.

4. The method of claim 1, wherein the comparing includes autocorrelating the normalized data set with the stored data set.

5. The method of claim 1, wherein:
   the stored data set is associated with an aggregated data set, the aggregated data set representing a plurality of users; and
   comparing the normalized data set to a stored data set includes identification of differences between the normalized data set and the stored data set.

6. The method of claim 1, wherein the plurality of GUI output card objects includes a recommended user action based on the comparison.

7. The method of claim 1, further including generating a new output card object based on the user data set update, wherein the second arrangement of the GUI output card objects includes replacing the GUI output card object associated with the completed status with the new output card object.

8. The method of claim 7, wherein:
   the new output card object is associated with a new card priority level; and
   the determination of the second arrangement of the GUI output card objects is further based on the new card priority level.

9. A system for facilitating data categorization and delivery, the system comprising:
   a memory;
   a processor;
   a receiving module to receive an input data set and sensor data associated with a user and to receive a user data set update;
   a normalizing module to normalize the input data set, the input data set including at least one input event;
   a comparison module to compare the normalized data set to a stored data set, the comparison indicating a relationship between the at least one input event in the normalized data set and at least one stored event in the stored data set;
   an output module to:
   generate a plurality of graphical user interface (GUI) output card objects based on the comparison, each of the plurality of GUI output card objects configured for display on a user device, each of the plurality of GUI output card objects having an associated card object priority level; and
   determine a first arrangement of the GUI output card objects based on the plurality of GUI output card objects and the received sensor data; and
   a card generation module to:
   present the plurality of GUI output card objects in the first arrangement within a GUI display, the first arrangement based on the plurality of GUI output card objects and the received sensor data;
   wherein:
   the user data set update received by the receiving module is based on a user interaction with a selected card object of the plurality of GUI output card objects;
   a completed status is associated with one of the plurality of GUI output card objects based on the user data set update;
   the output module is further to determine a second arrangement of the GUI output card objects based on the card object priority level associated with each of the plurality of GUI output card objects, the second arrangement excluding the GUI output card object associated with the completed status and including at least one revealed output card object not previously displayed within the first arrangement; and
   the card generation module is further to present a subset of the plurality of GUI output card objects in a second arrangement within the GUI display, the second arrangement based on the user data set update.

10. The system of claim 9, wherein the received user data set update is based on a GUI input associated with one of the plurality of GUI input objects.

11. The system of claim 9, wherein the comparison module is to cross-correlate the normalized data set with the stored data set.

12. The system of claim 9, wherein the comparison module is to autocorrelate the normalized data set with the stored data set.

13. The system of claim 9, wherein:
the stored data set is associated with an aggregated data set, the aggregated data set representing a plurality of users; and
the comparison module is to identify differences between the normalized data set and the stored data set.

14. The system of claim 9, wherein the plurality of GUI output card objects includes a recommended user action based on the comparison.

15. The system of claim 9, further including generating a new output card object based on the user data set update, wherein the second arrangement of the GUI output card objects includes replacing the GUI output card object associated with the completed status with the new output card object.

16. The system of claim 15, wherein
the new output card object is associated with a new card priority level; and
the determination of the second arrangement of the GUI output card objects is further based on the new card priority level.

17. A non-transitory machine-readable storage medium comprising a plurality of instructions that, in response to being executed on a computing device, cause the computing device to facilitate data categorization and delivery, with the plurality of instructions causing the computing device to:
receive an input data set and sensor data associated with a user;
normalize the input data set, the input data set including at least one input event;
compare the normalized data set to a stored data set, the comparison indicating a relationship between the at least one input event in the normalized data set and at least one stored event in the stored data set;
generate a plurality of graphical user interface (GUI) output card objects based on the comparison, the plurality of GUI output card objects for display on a user device, each of the plurality of GUI output card objects having an associated card object priority level;
determine a first arrangement of the GUI output card objects based on the plurality of GUI output card objects and the received sensor data;
present the plurality of GUI output card objects in the first arrangement within a graphical user interface (GUI) display, the first arrangement based on the plurality of GUI output card objects and the received sensor data;
receive a user data set update based on a user interaction with a selected card object of the plurality of GUI output card objects;
associate a completed status with one of the plurality of GUI output card objects based on the user data set update;
determine a second arrangement of the GUI output card objects based on the card object priority level associated with each of the plurality of GUI output card objects, the second arrangement excluding the GUI output card object associated with the completed status and including at least one revealed output card object not previously displayed within the first arrangement; and
present the second arrangement within the GUI display.

18. The machine-readable storage medium of claim 17, wherein the plurality of GUI output card objects includes a recommended user action based on the comparison.

19. The machine-readable storage medium of claim 17, further including generating a new output card object based on the user data set update, wherein the second arrangement of the GUI output card objects includes replacing the GUI output card object associated with the completed status with the new output card object.

20. The machine-readable storage medium of claim 19, wherein:
the new output card object is associated with a new card priority level; and
the determination of the second arrangement of the GUI output card objects is further based on the new card priority level.

* * * * *